US012725693B2

(12) United States Patent
Renisch et al.

(10) Patent No.: US 12,725,693 B2
(45) Date of Patent: Sep. 1, 2026

(54) METHODS AND SYSTEMS FOR SEQUENTIAL TRANSMISSION OF COMPRESSED MEDICAL IMAGE DATA TO A REMOTE SYSTEM

(71) Applicant: KONINKLIJKE PHILIPS N.V., Eindhoven (NL)

(72) Inventors: Steffen Renisch, Hamburg (DE); Thomas Netsch, Hamburg (DE); Dirk Schaefer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 315 days.

(21) Appl. No.: 18/524,542

(22) Filed: Nov. 30, 2023

(65) Prior Publication Data

US 2024/0177831 A1 May 30, 2024

(30) Foreign Application Priority Data

Nov. 30, 2022 (EP) .................................... 22210565

(51) Int. Cl.
*G16H 30/20* (2018.01)
*G06V 10/77* (2022.01)
(Continued)

(52) U.S. Cl.
CPC ......... *G16H 30/20* (2018.01); *G06V 10/7715* (2022.01); *G06V 10/82* (2022.01);
(Continued)

(58) Field of Classification Search
CPC ........ G16H 30/20; G16H 40/63; G16H 50/20; G16H 50/70; G06V 10/7715; G06V 10/82;
(Continued)

(56) References Cited

U.S. PATENT DOCUMENTS

| | | | | |
|---|---|---|---|---|
| 11,670,417 | B2 * | 6/2023 | Banerjee | G06V 10/82 702/19 |
| 2020/0250398 | A1 * | 8/2020 | Courtiol | G06V 10/82 |

(Continued)

FOREIGN PATENT DOCUMENTS

| | | |
|---|---|---|
| WO | WO2013072889 A1 | 5/2013 |
| WO | WO2021220008 A1 | 11/2021 |

OTHER PUBLICATIONS

Serych J. et al., "The JPEG Compression Algorithm", Wolfram Demonstrations Project, May 6, 2011. https://demonstrations.wolfram.com/JPEGCompressionAlgorithm/.

(Continued)

*Primary Examiner* — Juan M Guillermety

(57) ABSTRACT

The application describes various embodiments of a medical system, a computer program, and a method related to sequential transmission of compressed medical image data. As an example, a medical system comprising a local memory storing local machine executable instructions and a local computational system. Execution of the machine executable instructions further causes the computational system to: receive a feature vector descriptive of medical image data, wherein the feature vector is configured to be input into a decoder neural network, wherein the decoder neural network is configured to output an approximation of the medical image data when receiving at least a part of the feature vector as input, wherein the feature vector comprises a ranking assigning an importance to elements of the feature vector; and sequentially transmit portions of the feature vector to a remote computational system via a network connection, wherein the portions of the features vector with a higher importance are transmitted first.

18 Claims, 7 Drawing Sheets

(51) Int. Cl.
*G06V 10/82* (2022.01)
*H04N 19/136* (2014.01)
*H04N 19/42* (2014.01)

(52) U.S. Cl.
CPC .......... *H04N 19/136* (2014.11); *H04N 19/42* (2014.11); *G06V 2201/03* (2022.01)

(58) Field of Classification Search
CPC .. G06V 2201/03; H04N 19/136; H04N 19/42; G06N 3/0464; G06N 3/0495; G06N 3/084; G06N 3/088; G06N 3/09; G06N 3/0455; G06T 9/002
See application file for complete search history.

(56) References Cited

U.S. PATENT DOCUMENTS

| | | | | |
|---|---|---|---|---|
| 2020/0351509 | A1 | 11/2020 | Lee | |
| 2021/0027169 | A1 | 1/2021 | Kanan | |
| 2021/0374599 | A1* | 12/2021 | Kozloski | G06N 3/094 |
| 2023/0237089 | A1* | 7/2023 | Hu | G06V 10/806 707/718 |
| 2023/0252075 | A1* | 8/2023 | Habbecke | G06N 3/09 707/741 |
| 2024/0108276 | A1* | 4/2024 | Fuhrman | G06T 7/0012 |

OTHER PUBLICATIONS

Li M. et al., "Learning Convolutional Networks for Content-Weighted Image Compression", Proceedings of the IEEE Conference on Computer Vision and Pattern Recognition, pp. 3214-3223, 2018.

Kunwar S. et al., "Strategies in JPEG Compression Using Convolutional Neural Networks (CNN)", arXiv:2112.04500v1 [ eess.IV], Dec. 2021.

Alexandre D. et al., "An Autoencoder-Based Learned Image Compressor: Description of Challenge Proposal by NCTU", arxiv.org, Cornell University Library, 201 Olin Library Cornell University Ithaca, NY 14853, Feb. 20, 2019 (Feb. 20, 2019), XP081031130.

Sebai D. et al., "Semantic-Oriented Learning-Based Image Compression by Only-Train-Once Quantized Autoencoders", Signal, Image and Video Processing, [Online] vol. 17, No. 1, Apr. 29, 2022, pp. 285-293, XP093029571, London. Retrieved from the Internet: URL:https://link.springer.com/article/10.1007/s11760-022-02231-1/fulltext.html>.

Habibian A. et al., "Video Compression With Rate-Distortion Autoencoders", arxiv.org, Cornell University Library, 201 Olin Library Cornell University Ithaca, NY 14853, Aug. 14, 2019, XP081531236.

PCT International Search Report, International application No. PCT/EP2023/083287, Jan. 16, 2024.

* cited by examiner receiver
104
108
106'
120
122
132
134
140
142
144
146
transmitter
102
106
110
112
114
116
130
132
134
136
302
304
306
300

METHODS AND SYSTEMS FOR SEQUENTIAL TRANSMISSION OF COMPRESSED MEDICAL IMAGE DATA TO A REMOTE SYSTEM

FIELD

The embodiments described herein are related to medical imaging, in particular to the transmission of medical image data.

BACKGROUND

Various tomographic medical imaging techniques such as Magnetic Resonance Imaging (MRI). Computed Tomography. Positron Emission Tomography, and Single Photon Emission Tomography enable detailed visualization of anatomical structure of a subject. A common feature of these imaging modalities is that the volume of measurement data used to reconstruct a medical image may be quite large. Another common feature is that the storage of large numbers of reconstructed medical images may require a large storage volume.

International patent publication WO2021220008A1 discloses a computer-implemented method for lossy image or video compression, transmission and decoding, the method including the steps of: (i) receiving an input image at a first computer system: (ϋ) encoding the input image using a first trained neural network, using the first computer system, to produce a latent representation: (iii) quantizing the latent representation using the first computer system to produce a quantized latent: (iv) entropy encoding the quantized latent into a bitstream, using the first computer system: (v) transmitting the bitstream to a second computer system: (vi) the second computer system entropy decoding the bitstream to produce the quantized latent: (vii) the second computer system using a second trained neural network to produce an output image from the quantized latent, wherein the output image is an approximation of the input image.

SUMMARY

Various embodiments of the invention disclosed herein disclose a medical system, a computer program, and a method.

As mentioned above, large amounts of data to be transferred when performing a remote reconstruction of a medical image or when retrieving reconstructed medical images or records from a storage location or data warehouse. Embodiments may provide for a more robust means of transmitting medical image data to a remote location. Embodiments may possibly achieve this by receiving a feature vector descriptive of the medical image data and then transmitting portions of the feature vector with a higher importance first.

Various embodiments of the invention include a medical system that comprises a local memory storing local machine-executable instructions and a local computational system. Execution of the machine-executable instructions causes the computational system to receive a feature vector that is descriptive of medical image data. The feature vector may be described as encoding the medical image data or providing a compression of the medical image data. The feature vector is configured to be input into a decoder neural network. The decoder neural network is configured to output an approximation of the medical image data when receiving at least a part of the feature vector as input.

The feature vector comprises a ranking assigning an importance to elements of the feature vector. The ranking may be assigned in different ways. For example, the various elements or members of the feature vector may comprise a value which provides the ranking. In other cases, the feature vector could be binned into different bins or storage means or locations to store a discreetly assigned ranking. Execution of the machine-executable instructions further causes the computational system to sequentially transmit portions of the feature vector to a remote computational system via a network connection. The portions of the feature vector with a higher importance as assigned in the ranking are transmitted first. This embodiment may be beneficial because it may provide for a means of transmitting a portion of the feature vector in a means which enables a reconstruction of the approximation of the medical image data.

In one example the decoder neural network is a decoder portion of an autoencoder neural network. There may therefore be a corresponding encoder neural network that is the encoder portion of the autoencoder neural network. The feature vector may be the latent space of this autoencoder. As used herein, the terms decoder neural network may be replaced with decoder portion of the autoencoder. Also as used herein, the term encoder neural network may be replaced with encoder portion of the autoencoder.

Different types of autoencoders may be used to provide the encoder neural network and the decoder neural network. The encoder neural network and the decoder neural network may, for example, each be formed from multiple hidden layers that are a combination of convolutional layers, max pooling layers, batch normalization layers. ReLU layers and/or fully connected layers. The autoencoder may also be a variational autoencoder or a vector quantized autoencoder. However, skip connections across the bottleneck of the autoencoder (as are used e.g., by variants of the Densenet implementation may) not be used here since they effectively “cut short” the required feature abstraction (and the size reduction that comes along with it).

For example, the encoder neural network may comprise an input layer configured to receive the medical image data. The encoder neural network may then have multiple hidden layers formed from, for example, a combination of convolutional layers and/or fully connected layers. The output of the last of the hidden layers is then connected to an output layer configured for outputting the feature vector. The size of the feature vector is a choice which represents the degree of compression. In one case the size of the feature vector could be chosen such that it has a number of elements which is 30% (between 25% and 35%) of the number of elements in the medical image data. Because a neural network can be trained to reproduce specific types of data, accurate compression can be much higher than with algorithmic compression such as “zip.”

Another approach is to have the feature vector to have a number of elements closer in number to the number of elements in the original medical image data. If the decoder neural network is trained using dropout then the approximating of the medical image data provided when decompressing the feature vector may be robust with respect to missing or incomplete data.

In analogy with the example encoder neural network, the decoder neural network may comprise an input layer configured to receive the feature vector produced by the encoder neural network. The decoder neural network may then comprise multiple hidden layers formed, for example, from convolutional and/or fully connected layers. The last in the sequence of fully connected layers may be connected to an output layer of the decoder neural network which is configured to output an approximation of the medical image data.

The decoder neural network and the encoder neural network may be trained together. For example, the encoder neural network and the decoder neural network form an autoencoder with the feature vector being equivalent to a latent space vector. The pair of the encoder neural network and the decoder neural network may be trained by taking examples of medical image data and inputting them into the encoder neural network and receiving the feature vector. The feature vector is then input into the decoder neural network and its output is then compared to the original medical image data that was input into it.

To enable the decoder neural network to output approximation when only a portion of the feature vector is input, during training portions of the feature vector can be dropped out. For example, they can be set to zero of not a value. In some cases, during training the ranking can be assigned to the feature vector during the training. The elements to select for dropout may for example be those elements which have a lower ranking. This may provide for an encoder neural network pair and decoder neural network pair that have the ability to accurately approximate the medical image data with only a portion of the feature vector.

When the portions of the feature vector are transmitted to the remote computational system meta data descriptive of the medical image data may be optionally transmitted also. If the medical image data is measurement data from a medical imaging system or tomographic medical imaging system the metadata may include a description or code which describes how to reconstruct the medical image data into a medical image.

In another embodiment the local memory further comprises an encoder neural network. Execution of the local machine-executable instructions further causes the local computational system to receive the medical image data. Execution of the local machine-executable instructions further causes the local computational system to receive the feature vector in response to inputting the medical image data into the encoder neural network. Execution of the local machine-executable instructions further causes the local computational system to determine and assign the ranking to the elements of the feature vector.

In another embodiment the determination of the ranking comprises determining a magnitude of the elements of the feature vector and then assigning a ranking to the elements of the feature vector that increases when the magnitude increases. The ranking may for example be a numerical value which is assigned to the elements of the feature vector. In other cases the ranking may be a discreet assignment that may be a value or it may also be determined by a location in a memory or storage. For example, elements of the feature vector which are assigned a particular ranking may be grouped or stored together. This embodiment may provide for an efficient means of assigning the ranking to the elements of the feature vector.

In another embodiment, the local memory further comprises an importance map neural network that is configured for receiving the medical image data as input and in response providing as output an assignment of the ranking to the elements of the feature vector. Execution of the local machine-executable instructions further comprises receiving the ranking of the elements of the feature vector from the importance map neural network in response to inputting the medical image data into the importance map neural network. This embodiment may for example be beneficial because it may provide for a means of assigning an importance to various elements of the feature vector that are not dependent upon the magnitude of the element alone. This may provide for a more accurate assignment.

The importance map neural network may for example be formed from several hidden layers that are e.g. convolutional layers, batch normalization layers. ReLU layers and/or fully connected layers. Since this importance map network is a classification/regression network independent of the decoder part of the autoencoder (since its purpose is the assignment of a ranking to the elements of the feature vector), it may also include "skip connections", so Densenet-like architectures can be used for this purpose.

It is noteworthy however that training of the importance map requires data annotations indicating the regions of the image that are of diagnostic relevance. Those may be generated e.g. by manual annotations, or by extraction of the relevant regions from radiologist's reports by means of natural language processing. In any case these data may not be very abundant, so that network architectures requiring fewer training data (e.g. EfficientNet-like implementations) may be favorable.

The training of the importance map network may include several reconstructions of an image from a feature vector using the decoder part of the autoencoder, where some noise is added to the individual components with an amplitude corresponding to the inverse (or inverse squared) output of the importance map. The loss function would then comprise the average of the differences of the reconstructed and the original images, where the annotated regions are weighted higher than the other regions, using some metric (e.g. the L2 norm).

In another embodiment the importance map neural network is implemented as a separate neural network. As an example, the importance map neural network comprises an input layer configured to receive the original medical image data. There are then a number of hidden layers, for example, comprising convolutional and/or fully connected layers. The last in the sequence of hidden layers is then connected to an output layer configured to assign the ranking to each element of the feature vector.

In another embodiment the importance map neural network is implemented as a portion of the encoder neural network. For example, the importance map neural network may be several convolutional layers that are either separate or share input layers with the encoder neural network. As an example, the importance map neural network comprises a connection between one of the hidden layers of the encoder neural network and additional hidden layers belonging to the importance neural network. The additional hidden layers could, for example. Be convolutional and/or fully connected layers. The last in the sequence of hidden layers is then connected to an output layer configured to assign the ranking to each element of the feature vector.

In another embodiment the ranking comprises an array of values assigning the ranking to the elements of the feature vector. In this case. The ranking would then be an assignment of which elements would be transmitted first.

In another embodiment the ranking comprises assignment of the elements of the feature vector to a discreet number of storage locations. The discreet number of storage locations have different data retrieval latencies and a lower retrieval latency is equivalent to a higher ranking. This embodiment may be particularly beneficial because it may provide for an efficient means of using memory locations with different latencies. For example. The most important data has the lower data latency and is therefore available earlier for transmission. In some cases it may also provide an economic benefit as data may be stored in data warehouses or other storage locations on different media types or storage mediums. The more important data may therefore be available using a storage device which has the data available more readily and for example. May have higher costs. The less important data may be stored at a location or storage facility which has larger latency times. This for example may provide for a means of not only providing important parts used for reconstructing an image more rapidly but may also provide for reduced costs in storage.

In another embodiment the feature vector is received by retrieving the portion of the feature vector from the discreet number of storage locations according to the ranking. In this case, the portions of the feature vector which have the higher ranking are stored in locations with a lower latency and are retrieved first. As was mentioned above. This may provide for various economies of speed and cost.

In another embodiment the medical system further comprises a remote memory storing machine-executable instructions and the decoder neural network. As was mentioned before, the encoder neural network and the decoder neural network may in essence form an autoencoder neural network. The medical system further comprises a remote computational system. Execution of the remote machine-executable instructions causes the remote computational system to sequentially receive the portions of the feature vector via the network connection. Execution of the remote machine-executable instructions further causes the remote computational system to assemble received portions of the feature vector into the part of the feature vector.

Execution of the remote machine-executable instructions further causes the remote computational system to receive an approximation of the medical image data in response to inputting the part of the feature vector into the decoder neural network. The received portions of the feature vector are input into the decoder neural network before all portions of the feature vector have been received. This for example may provide a means of providing an initial approximation of the medical image data. In some cases, this approximation of the medical image data may for example enable an algorithm to begin a reconstruction process before all of the medical image data is available. In other cases, this also enables reconstruction of the medical image data if the transmission of the feature vector is interrupted.

In another embodiment the medical image data is measurement data. Execution of the remote machine-executable instructions further causes the remote computational system to reconstruct a preliminary medical image from the medical image data before all portions of the feature vector have been received.

In different examples the medical image data may take different forms. In one instance it may be measurement data from a magnetic resonance imaging system. In this case the measurement data could be k-space data. In other examples, for example for parallel imaging magnetic resonance imaging protocols there are individual coil images produced for each coil element. In this case the preliminary medical image may be a collection or a number of individual coil images from a parallel imaging magnetic resonance imaging profile.

In yet other cases the preliminary medical image may be data from a Compute Tomography (CT) or Cone Beam Computed Tomography (CBCT) system. For example, they could be CT profiles or CBCT images.

In another embodiment the medical image data is a medical image. Execution of the machine-executable instructions further causes the computational system to render the approximation of the medical image. This for example may be particularly useful in cases where the feature vector is ranked by distributing it into different bins or different storage locations with different latencies. This for example may enable the recall of data and provide for an initial reconstruction which can be used to evaluate if it is desired to retrieve all of the data.

In another embodiment the assembly of the received portions of the feature vector, the approximation of the medical image data and the rendering of the approximation of the medical image data is repeated multiple times before reception of all portions of the feature vector have been received at the remote computational system. Execution of the remote machine-executable instructions further causes the remote computational system to receive a halt transmission instruction in response to displaying the rendering of the approximation of the medical image data and to transmit the halt transmission instruction to the local computational system via the network connection.

Execution of the local machine-executable instructions further causes the local computational system to receive the halt transmission instruction via the network connection and then to halt the transmission of the portions of the feature vector in response to receiving the halt transmission instruction. This embodiment may be particularly beneficial in using the data volume transmitted between the local computational system and the remote computational system when it is not necessary to transmit the complete feature vector.

Various embodiments of the invention include a medical system that comprises a remote memory storing remote machine-executable instructions and a decoder neural network. The decoder neural network is configured to output an approximation of medical image data in response to receiving at least a part of a feature vector as input. The medical system further comprises a remote computational system. Execution of the remote machine-executable instructions causes the remote computational system to sequentially receive portions of the feature vector via the network connection. Execution of the remote machine-executable instructions further causes the remote computational system to assemble the received portions of the feature vector into the part of the feature vector. Execution of the remote machine-executable instructions further causes the remote computational system to receive an approximation of the medical image data in response to inputting the part of the feature vector into the decoder neural network. The part of the feature vector is input into the decoder neural network before all portions of the feature vector have been received.

Various embodiments of the invention include a computer program that comprises local machine-executable instructions for execution by a local computational system. Execution of the machine-executable instructions causes the computational system to receive a feature vector descriptive of medical image data. The feature vector is configured to be input into a decoder neural network. The decoder neural network is configured to output an approximation of medical image data when receiving at least a part of the feature vector as input. The feature vector comprises a ranking assigning an importance to elements of the feature vector. Execution of the machine-executable instructions further causes the local computational system to sequentially transmit portions of the feature vector to a remote computational system via a network connection. The portions of the feature vector with higher importance are transmitted first.

Various embodiments of the invention include a method. The method comprises receiving a feature vector descriptive of medical image data via a local computational system. The feature vector is configured to be input into a decoder neural network. The decoder neural network is configured to output an approximation of medical image data when receiving at least a part of the feature vector as input. The feature vector comprises a ranking assigning an importance to elements of the feature vector. The method further comprises sequentially transmitting portions of the feature vector to a remote computational system via a network connection by the local computational system. The portions of the feature vector with a higher importance are transmitted first.

The method further comprises sequentially receiving the portions of the feature vector via the network connection by the remote computational system. The method further comprises assembling received portions of the feature vector into the part of the feature vector by the remote computational system. The method further comprises receiving an approximation of the medical image data in response to inputting the part of the feature vector into a decoder neural network by the remote computational system. The received portions of the feature vector are input into the decoder neural network before all portions of the feature vector have been received.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit." "module" or "system." Furthermore, aspects of the present invention may take the form of a computer program product embodied in one or more non-transient computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to a floppy disk, a magnetic hard disk drive, a solid state hard disk, flash memory, a USB thumb drive. Random Access Memory (RAM). Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the embodiments of the invention are described with reference to flowchart illustrations and/or block diagrams of methods, apparatus (systems) and computer program products. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a computational system of a general-purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include but are not limited to a universal serial bus. IEEE 1394 port, parallel port. IEEE 1284 port, serial port. RS-232 port. IEEE-488 port. Bluetooth connection. Wireless local area network connection. TCP/IP connection. Ethernet connection, control voltage interface. MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to a computer monitor, a television screen, a touch screen, tactile electronic display. Braille screen. Cathode ray tube (CRT). Storage tube. Bi-stable display. Electronic paper. Vector display. Flat panel display. Vacuum fluorescent display (VF). Light-emitting diode (LED) displays. Electroluminescent display (ELD). Plasma display panels (PDP). Liquid crystal display (LCD). Organic light-emitting diode displays (OLED), a projector, and Head-mounted display.

Measurement data is defined herein as being recorded measurements made by a tomographic medical imaging system descriptive of a subject. The medical imaging data may be reconstructed into a medical image. A medical image is defined herein as being the reconstructed two- or three-dimensional visualization of anatomic data contained within the medical imaging data. This visualization can be performed using a computer.

The term medical image data may refer to either measurement data or to a medical image depending upon the context.

BRIEF DESCRIPTION OF THE DRAWINGS

In the following preferred embodiments of the invention will be described, by way of example only, and with reference to the drawings in which.

DETAILED DESCRIPTION OF EMBODIMENTS

Like numbered elements in these FIGS. are either equivalent elements or perform the same function. Elements which have been discussed previously will not necessarily be discussed in later FIGS. if the function is equivalent.

Figure 1:
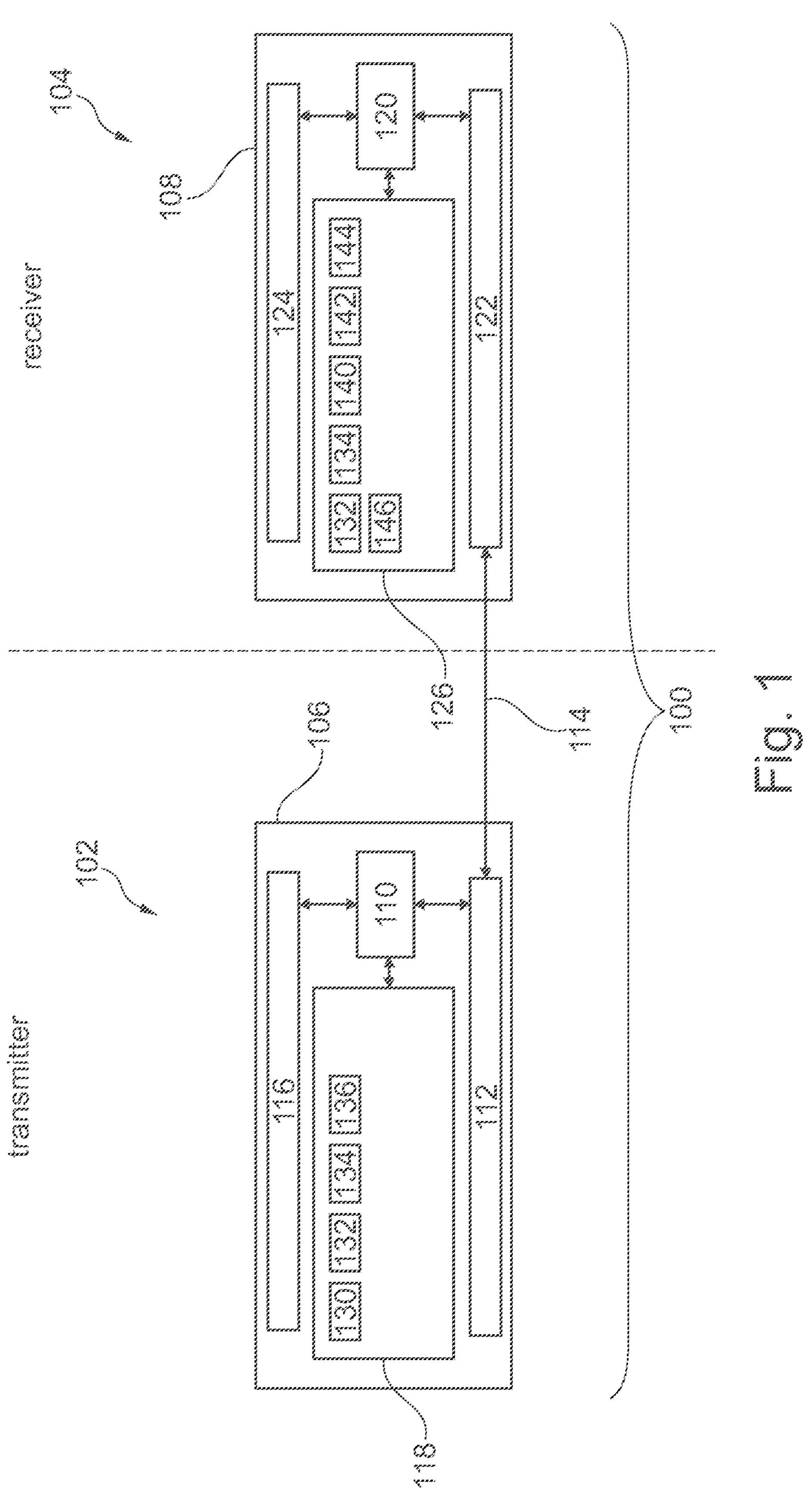
FIG. 1 illustrates an example of a medical system.

FIG. 1 illustrates an example of a medical system 100. The medical system 100 comprises a transmitter portion 102 and a receiver portion 104. The transmitter portion 102 in this example is shown as comprising a local computer 106. The local computer 106 is intended to represent one or more computers. The local computer 106 is shown as comprising a local computational system 110. The local computational system 110 is intended to represent one or more computational or computer cores. The local computational system 110 is shown as being connected to a local network interface 112, which is used to form a network connection 114 with the remote computer 108. The local computer 106 is further shown as comprising an optional local hardware interface 116. The local hardware interface 116, if it is present, may be used to operate and control other components of the transmitter portion 102. The local computer 106 is further shown as comprising a local memory 118. The local memory 118 is intended to represent various types of memories or storage that is accessible to the local computational system 110.

The remote computer 108 is shown as containing a remote computational system 120. The remote computational system 120 is intended to represent one or more computational systems or computer cores. The remote computational system 120 is shown as being in connection with an optional user interface 124 as well as a remote network interface 122. The local network interface 112 and the remote network interface 122 are used to form the network connection 114. The remote computational system 120 is shown as being in further connection with a remote memory 126. The remote memory 126 is intended to represent the various types of memory and storage which are accessible to the remote computational system 120. The local memory 118 as well as the remote memory 126 may for example be examples of a non-transitory storage medium.

The local memory 118 is shown as containing local machine-executable instructions 130. The local machine-executable instructions contain instructions which enable the local computational system 110 to perform basic data analysis and data processing tasks. The local memory 118 is further shown as containing a first portion of a feature vector 132, a second portion of a feature vector 134, and a third portion of a feature vector 136.

The remote memory 126 is shown as containing the first portion of the feature vector, and the second portion of the feature vector 134. The remote memory 126 is further shown as containing remote machine-executable instructions 140. The remote machine-executable instructions 140 enable the remote computational system 120 to perform basic data processing and data manipulation tasks. The remote memory 126 is further shown as containing a decoder neural network 142 that is configured to output an approximation of medical image data in response to receiving at least a portion of the feature vector 132, 134, 136. The memory 126 is shown as containing an incomplete feature vector 144 that has been assembled from the first portion of the feature vector 132 and the second portion of the feature vector 134. The remote memory 126 is further shown as containing an approximation of the medical image data 146 that was received from the decoder neural network 142 in response to inputting the incomplete feature vector 144.

Figure 2:
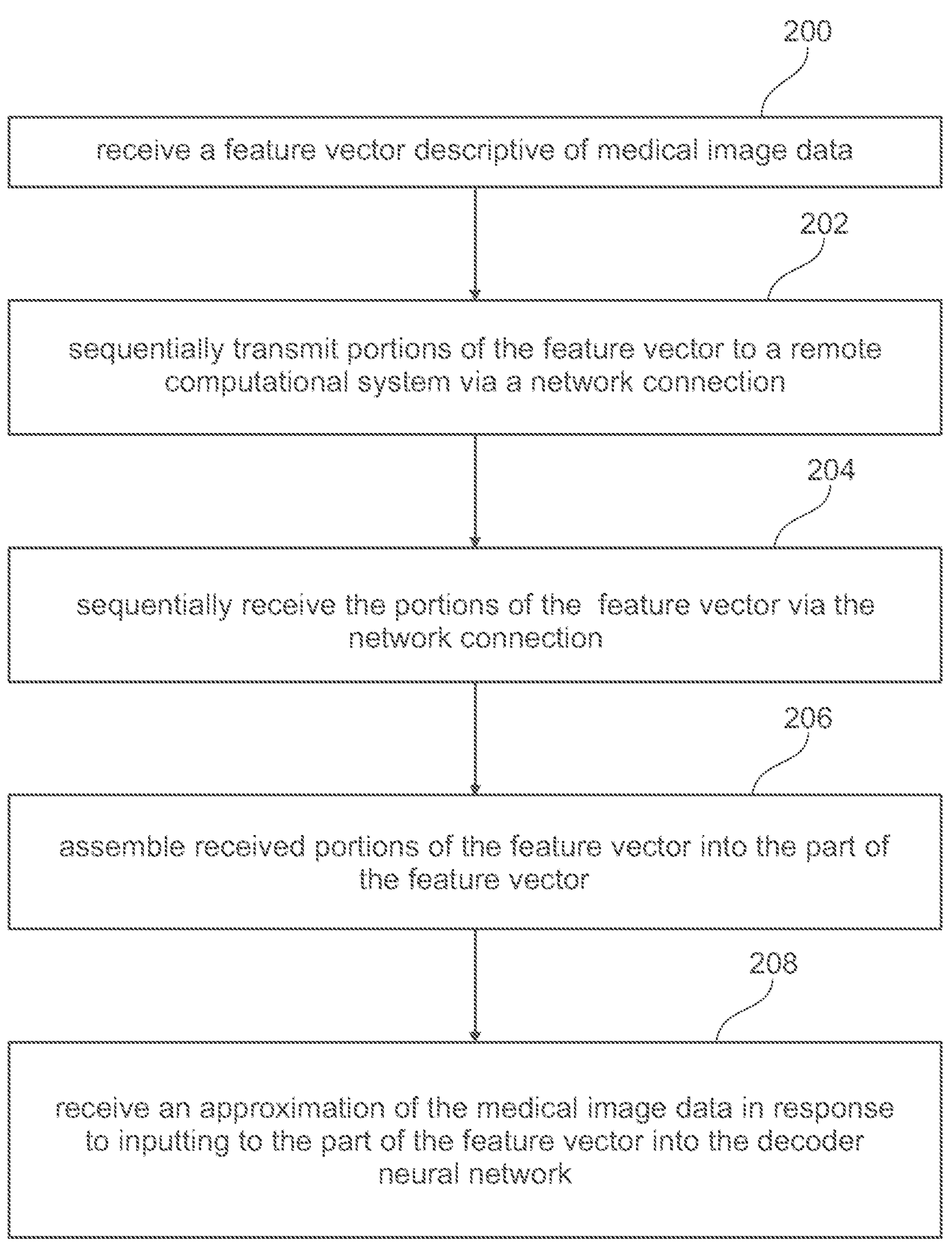
FIG. 2 shows a flow chart which illustrates a method of using the medical system of FIG. 1 or FIG. 3.

FIG. 2 shows a flowchart which illustrates a method of operating the medical system 100 of FIG. 1. First, in step 200, a feature vector 132, 134, 136 is received which is descriptive of medical image data. Next, in step 202, the portions of the feature vector 132, 134, 136 are transmitted to the remote computational system 120 via the network connection 114. In this example, the feature vector has been divided into three portions 132, 134 and 136. This assignment of the different parts of the feature vectors to these different portions 132, 134, 136 is equivalent to assigning a ranking which assigns an importance to the various elements of the feature vector. For example, the elements of the feature vector in the first portion. 132, are considered to be the most important or relevant parts of the feature vector. The second portion. 134, contains the second most important and the third portion. 136, contains the third most important portion.

The division of the feature vector into three portions 132, 134, 136 is arbitrary. There may be any number of portions which the feature vector is divided into. In some examples the feature vector may be accompanied by an additional vector which assigns a numbering or ranking to the individual elements. In this particular example the elements of the feature vector in the first portion. 132, are transmitted first. It can be seen that in this example just the first portion. 132, and the second portion. 134, have been transmitted to the receiver portion 104.

After step 202 is performed the method proceeds to step 204, where the portions of the feature vector 132, 134 are received by the remote computational system 120 via the network interface 114. Then, in step 206, the received portions 132, 134 of the feature vector are assembled into the part of the feature vector. In this case the part of the feature vector is the incomplete feature vector 144. Next, in step 208, the approximation of the medical image data 146 is received in response to inputting the part of the feature vector 144 into the decoder neural network 142.

Figure 3:
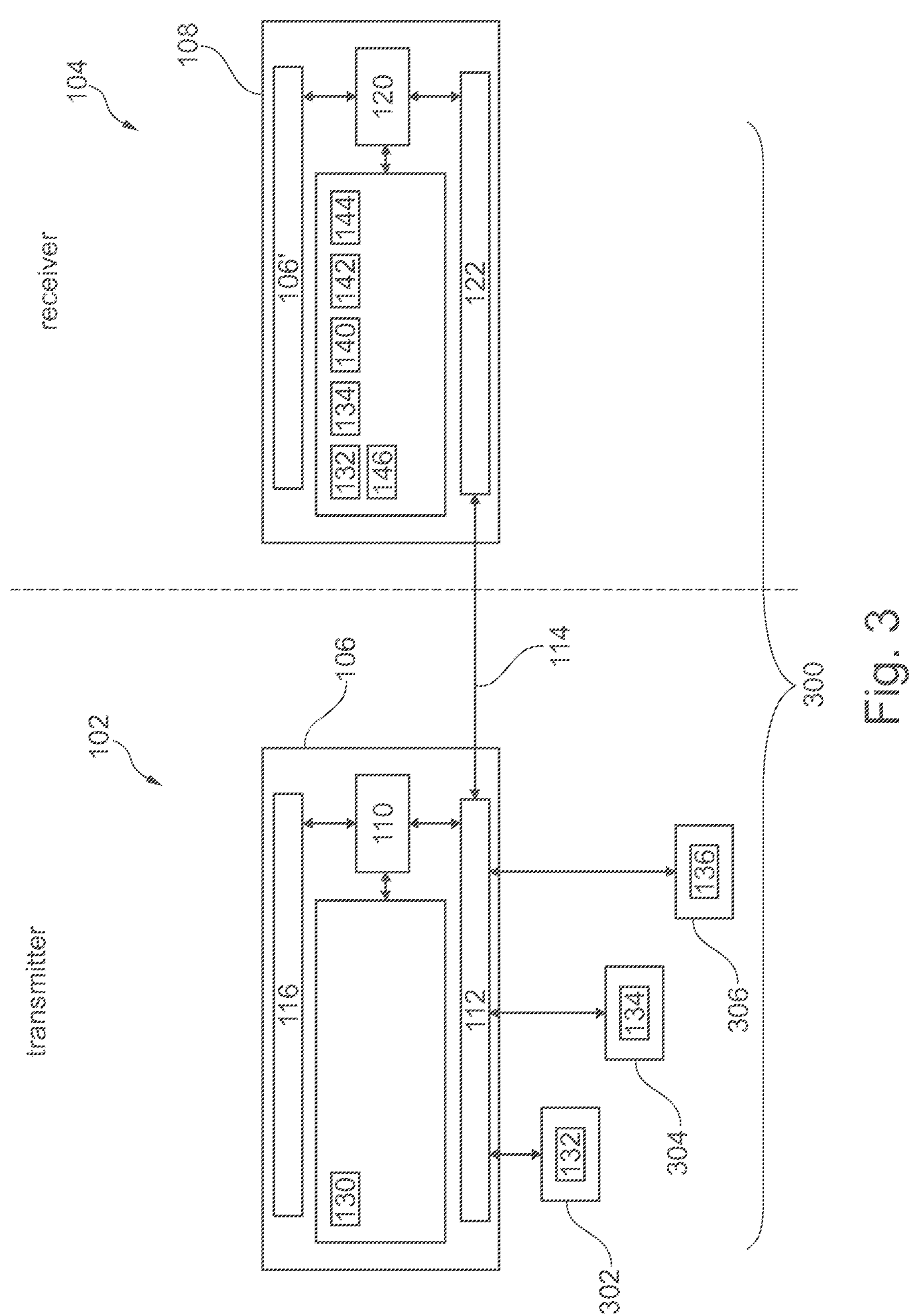
FIG. 3 illustrates a further example of a medical system.

FIG. 3 illustrates a further example of a medical system 300. The medical system 300 depicted in FIG. 3 is similar to the medical system 100 depicted in FIG. 1. In the medical system 300 the portions 132, 134, 136 of the feature vector are stored in different storage locations 302, 304, 306. In the FIG. it can be seen that the first portion of the feature vector 132 is stored in a first storage location 302. The second portion. 134, of the feature vector is stored in a second storage location 304. The third portion of the feature vector. 136, is stored in a third storage location 306. The first storage location 302 has the lowest latency and the third storage location 306 has the longest latency. The second storage location 304 has a latency which is intermediate to the latency of the first storage location 302 and the third storage location 306. This arrangement may be useful in several situations. As it is desirable to transmit the most important elements of the feature vector first, the lower latency of the first storage location 302 may enable more rapid transmission of the first portion of the feature vector 132.

The portions of the feature vector may therefore be retrieved and then transmitted in the order of importance. In this example, as soon as the portion of the feature vector 132 is received, it is automatically transmitted by the local computational system 110 to the remote computational system 120 via the network interface 114. Another situation where this may be useful is that in cloud and other types of commercially available storage, the latency of the storage location may determine the price. If this is the case for example illustrated in FIG. 3, then the most important portions of the medical image data are available rapidly in the first storage location 302. In some applications it may not be necessary to provide the third portion of the feature vector 136 or even the second portion of the feature vector 134. This may therefore enable a cost saving on data structures such as image or raw data used to reconstruct medical images. Data structures may be very large, and it may be desirable to have only a portion of them accessible rapidly.

Figure 4:
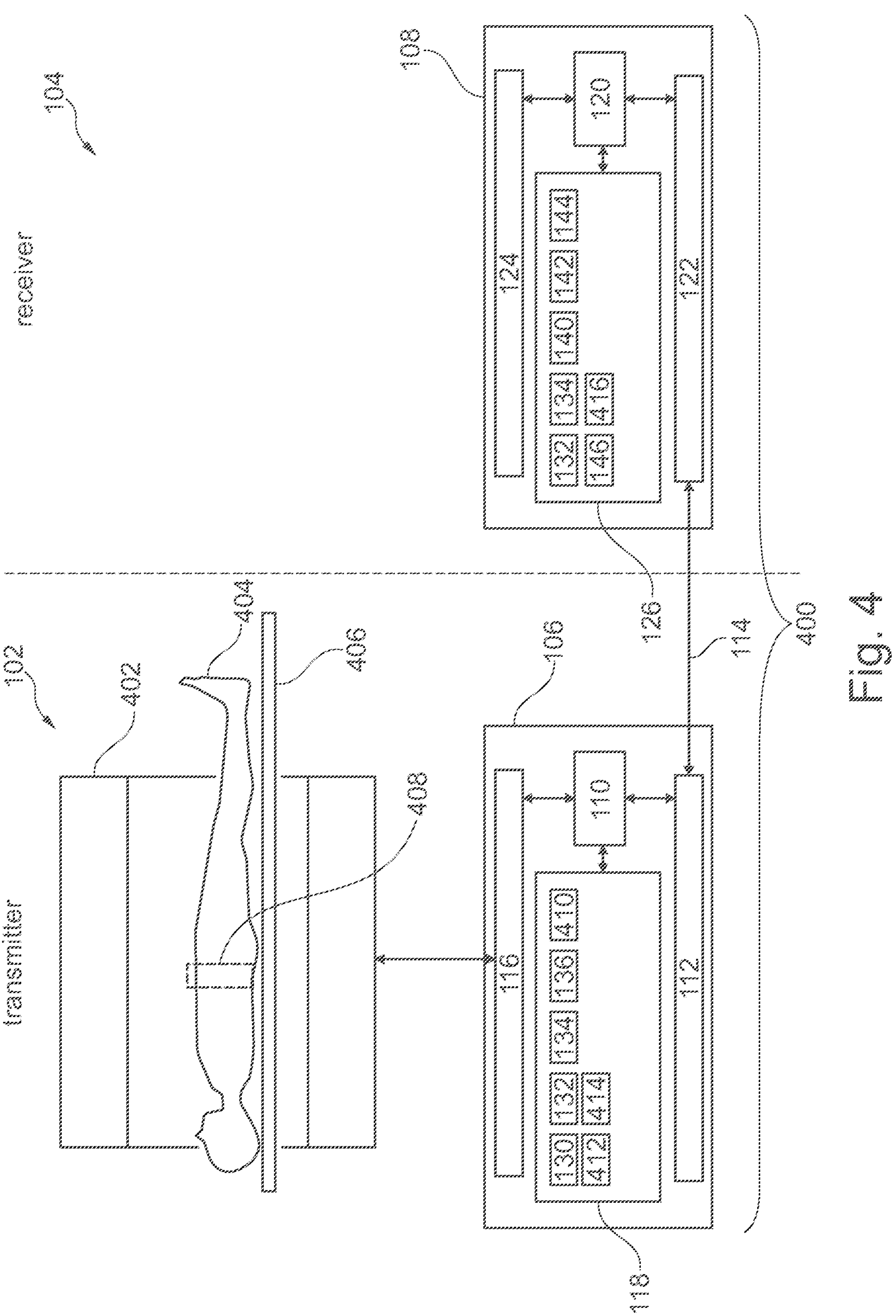
FIG. 4 illustrates a further example of a medical system.

FIG. 4 shows a further example of the medical system 400. The medical system 400 is similar to that depicted in FIG. 1 except that it additionally comprises a medical imaging system 402. The medical imaging system 402 is intended to represent various types of topographic medical imaging systems. The apparatus and methods depicted herein are particularly applicable to computed tomography.

A subject 404 is shown as reposing on a subject support 406. A portion of the subject 404 is shown as being within an imaging zone 408 of the medical imaging system 402. The local memory 118 is shown as additionally containing medical image data 410. In this case it is the raw measurement data acquired by the medical imaging system 402. The measurement data may for example be k-space data from a magnetic resonance imaging system. In other examples, the data is CT-profiles from a CT system or images from a CBCT system.

The local memory 118 is further shown as containing an encoder neural network 412. The local memory 118 is further shown as containing a feature vector 414 that was received in response to inputting the medical image data 410 into the encoder neural network 412. The feature vector 414 in this case has been divided into the first portion of the feature vector 132, the second portion of the feature vector 134, and the third portion of the feature vector 136. This may be done for example using an importance map neural network or by taking the elements of the feature vector which has the largest magnitude.

In this example, again only the first portion of the feature vector 132 and the second portion of the feature vector 134 have been transmitted to the remote computational system 120. As in the previous example, this has been used to provide the approximation of medical imaging data 146. In this particular example it is an approximation of the measurement data acquired by the medical imaging system 402. The memory 126 is then further shown as containing a preliminary medical image 416 that has been reconstructed from the approximation of medical image data 146.

Figure 5:
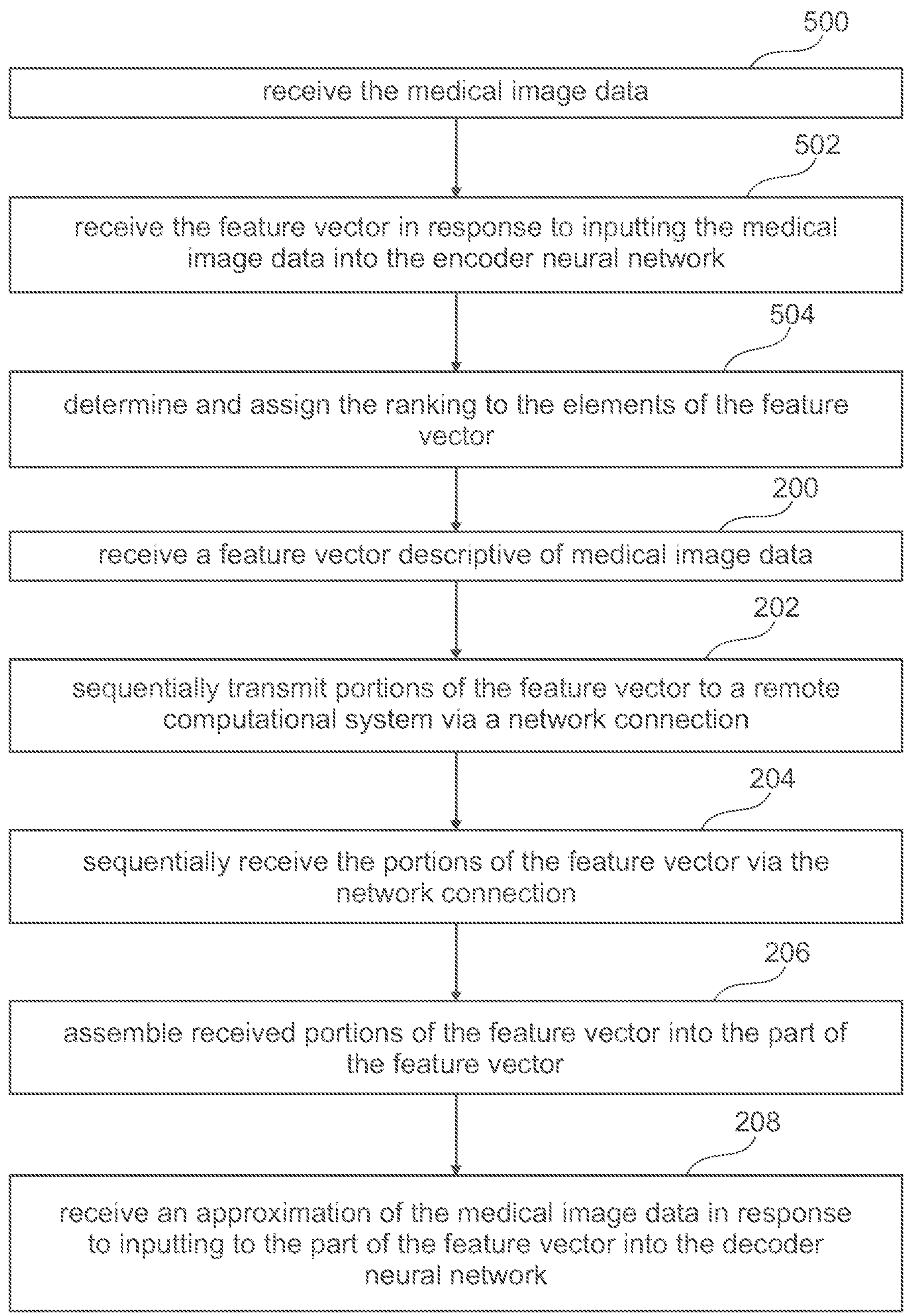
FIG. 5 shows a flow chart which illustrates a method of using the medical system of FIG. 4.

FIG. 5 shows a flowchart which illustrates a method of operating the medical system 400 of FIG. 4. First, in step 500, the medical image data 410 is received. In this case, this may include controlling the medical imaging system 402 to acquire the medical image data or measurement data. Next, in step 502, the feature vector 414 is received in response to inputting the medical image data 410 into the encoder neural network 412. Next, in step 504, the ranking of the elements of the feature vector 414 are determined and assigned. In this particular example this was done by binning the different elements of the feature vector 414 into the first portion 132, the second portion 134, or the third portion 136 of the feature vector. After step 504 is performed steps 200, 202, 204, 206, and 208 are performed as was illustrated in FIG. 2.

Figure 6:
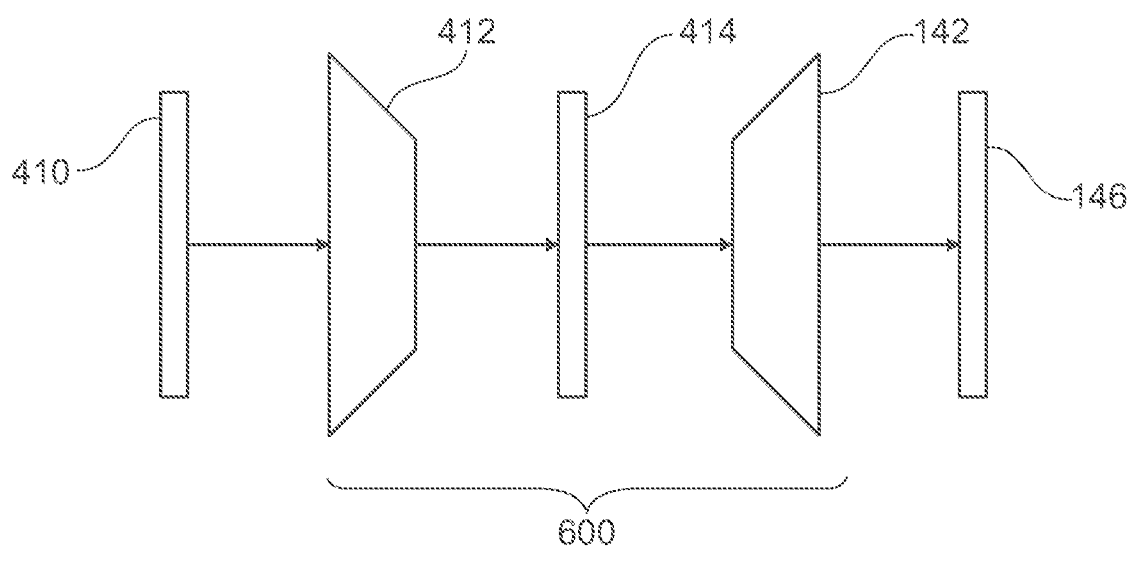
FIG. 6 illustrates an example of an encoder neural network and a decoder neural network.

FIG. 6 illustrates the functionality or the inoperability of the encoder neural network 412 and the decoder neural network 142. In this example they are arranged together as a functional autoencoder 600. In many instances, the encoder neural network 412 and the decoder neural network 142 would be constructed by taking a standard autoencoder neural network and then breaking them apart into two separate neural networks after training has been completed. In this example, the medical imaging data 410 is shown as being input into the encoder neural network 412 which then produces a feature vector 414. The feature vector 414 is a latent space vector for the autoencoder 600. When the feature vector 414 is input into the decoder neural network 142 an approximation of the medical image data 146 is output. During training elements of the feature vector 414 may be dropped out to train the decoder neural network 142 to be able to reconstruct the approximation of the medical image data 146 with only a portion of the feature vector 414 or missing elements.

Figure 7:
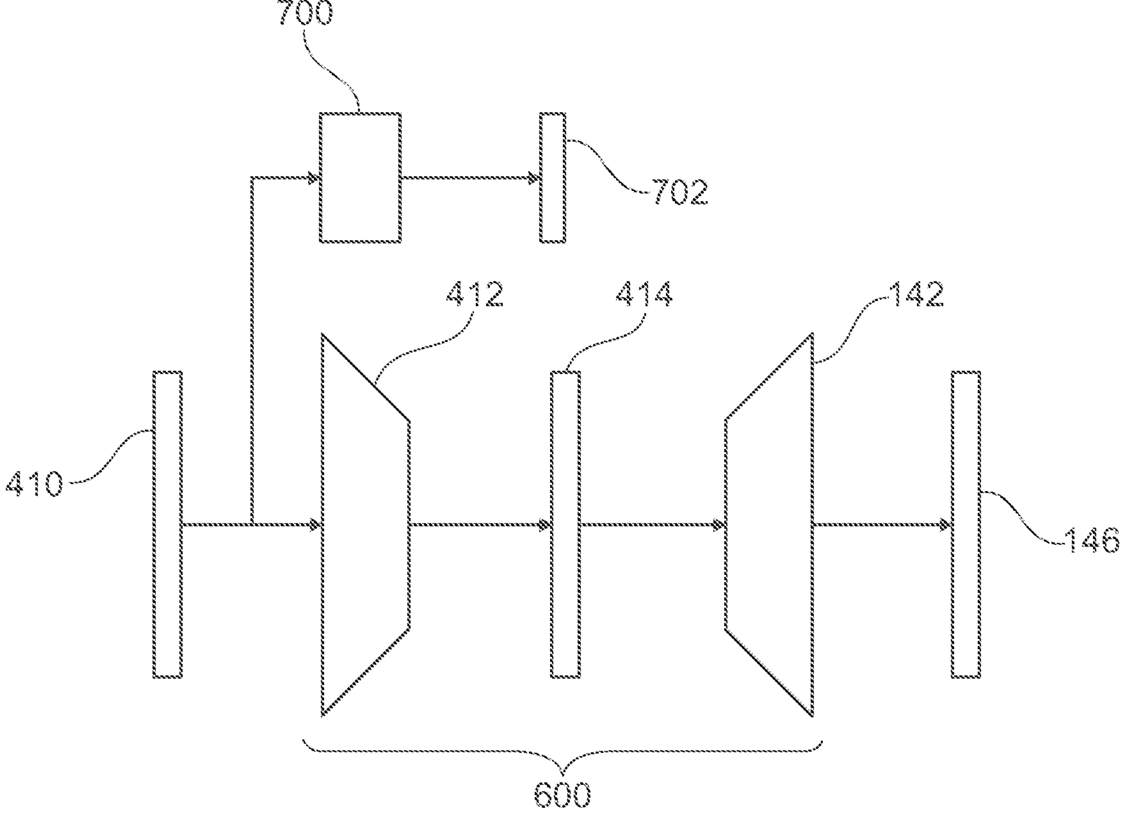
FIG. 7 illustrates a further example of an encoder neural network and a decoder neural network.

FIG. 7 shows a modification of the arrangement of neural networks illustrated in FIG. 6. In the example shown in FIG. 7 the autoencoder structure 600 is still shown. However, in this case, the medical image data 410 is put into an importance map neural network 700 that outputs a ranking 702 of the various elements of the feature vector 414. This ranking 702 can be used to sort or assign a ranking to individual elements. For example, the ranking 702 could be used to divide the feature vector 414 into the first portion 132, the second portion 134, and the third portion 136 as was illustrated in the previous examples. The importance map neural network could for example be formed from several convolutional or fully connected layers connected to an output layer. The output layer being configured assign a ranking to the elements of the feature vector.

Figure 8:
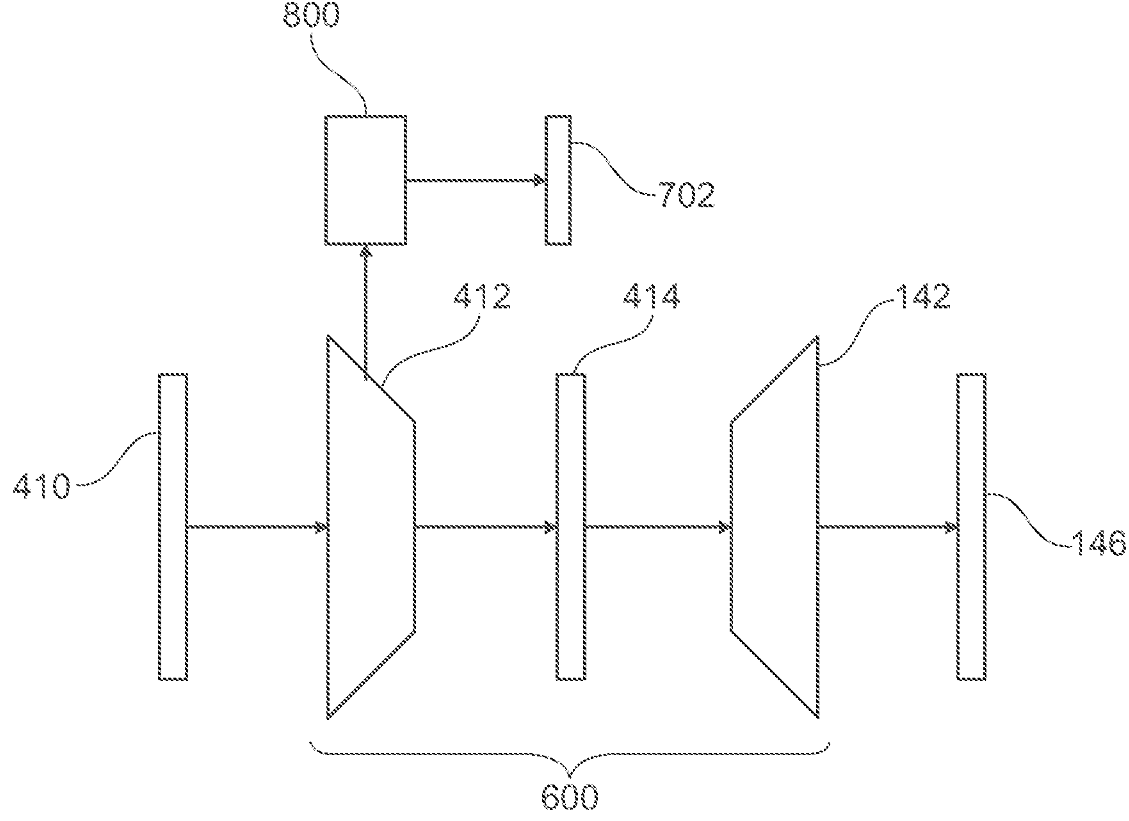
FIG. 8 illustrates a further example of an encoder neural network and a decoder neural network.

FIG. 8 shows a modification of the arrangement of neural networks illustrated in FIG. 7. In FIG. 7 there was a completely separate neural network 700 that was used to provide the rankings 702. In this example, there are importance map neural network layers 800 that are connected to a layer within the decoder neural network 412. For example, there could be several convolutional layers used to form the importance map neural network layer 800, which are connected before the output layer of the encoder neural network 412. The arrangement in FIG. 8 shows an alternative way of incorporating the generation of the ranking 702 into the encoder neural network 412.

While various embodiments of the invention have been illustrated and described in detail in the drawings and foregoing description, such illustration and description are to be considered illustrative or merely examples and not restrictive: the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be beneficial. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

Various embodiments of the invention also relate to a computer program comprising instructions which, when the program is executed by a computer, cause the computer to carry out any of the above method steps described above.

Various embodiments of the invention also relate to a computer-readable medium comprising instructions which, when executed by a computer, cause the computer to carry out any of the above method steps described above.

REFERENCE SIGNS LIST

100 medical system
102 transmitter portion
104 receiver portion
106 local computer
108 remote computer
110 local computational system
112 local network interface
114 network connection
116 local hardware interface
118 local memory

120 remote computational system
122 remote network interface
124 user interface
126 remote memory
130 local machine executable instructions
132 first portion of feature vector
134 second portion of feature vector
136 third portion of feature vector
140 remote machine executable instructions
142 decoder neural network
144 incomplete feature vector
146 approximation of medical image data
200 receive a feature vector descriptive of medical image data, wherein the feature vector is configured to be input into a decoder neural network
202 sequentially transmit portions of the feature vector to a remote computational system via a network connection
204 sequentially receive the portions of the feature vector via the network connection
206 assemble received portions of the feature vector into the part of the feature vector
208 receive an approximation of the medical image data in response to inputting to the part of the feature vector into the decoder neural network
300 medical system
302 first storage location
304 second storage location
306 third storage location
400 medical system
402 medical imaging system
404 subject
406 subject support
408 imaging zone
410 medical image data
412 encoder neural network
414 feature vector
416 preliminary medical image
500 receive the medical image data
502 receive the feature vector in response to inputting the medical image data into the encoder neural network
504 determining and assigning the ranking to the elements of the feature vector
600 functional autoencoder
700 importance map neural network
702 ranking
800 importance map neural network layers

The invention claimed is:

1. A medical system comprising:

a local memory storing local machine executable instructions and a local computational system, wherein execution of the machine executable instructions causes the computational system to:

receive a feature vector descriptive of medical image data, wherein the feature vector is configured to be input into a decoder neural network being a decoder portion of an autoencoder, wherein the decoder neural network is configured to output an approximation of the medical image data when receiving at least a part of the feature vector as input, wherein the feature vector comprises a ranking assigning an importance to each of a plurality of elements of the feature vector, wherein one or more of the plurality of elements are assigned a ranking of higher importance than one or more other of the plurality of elements, wherein the ranking comprises an assignment of the elements of the feature vector to a discrete number of storage locations, wherein the discrete number of storage locations have different data retrieval latencies, and wherein a lower data retrieval latency is equivalent to a higher ranking; and sequentially transmit portions of the feature vector to a remote computational system via a network connection, wherein the portions of the features vector with a higher importance are transmitted first, wherein the local memory further comprises an encoder neural network being an encoder portion of the autoencoder;

wherein execution of the local machine executable instructions further causes the local computational system to:

receive the medical image data;

receive the feature vector in response to inputting the medical image data into the encoder neural network, wherein the feature vector is received by retrieving the portions of the feature vector from the discrete number of storage locations according to the ranking; and determine and assign the ranking to the elements of the feature vector.

2. The medical system of claim 1, wherein the determination of the ranking comprises:

determining a magnitude of the elements of the feature vector; and assigning a ranking to the elements of the feature vector that increases when the magnitude increases.

3. The medical system of claim 1, wherein the local memory further comprises an importance map neural network configured for receiving the medical image data as input and in response providing as output an assignment of the ranking to the elements of the feature vector, wherein execution of the local machine executable instructions further comprises receiving the ranking of the elements of the feature vector from the importance map neural network in response to inputting the medical image data into the importance map neural network.

4. The medical system of claim 3, wherein the importance map neural network is implemented as any one of the following: incorporated into the encoder neural network and as a separate neural network.

5. The medical system of claim 1, wherein the ranking comprises an array of values that assigns the ranking to the elements of the feature vector.

6. The medical system of claim 1, wherein the medical system further comprises:

a remote memory storing remote machine executable instructions and the decoder neural network; and a remote computational system, wherein execution of the remote machine executable instructions causes the remote computational system to:

sequentially receive the portions of the feature vector via the network connection;

assemble received portions of the feature vector into the part of the feature vector; and receive an approximation of the medical image data in response to inputting to the part of the feature vector into the decoder neural network, and wherein the received portions of the feature vector is input into the decoder neural network before all portions of the feature vector have been received.

7. The medical system of claim 6, wherein the medical image data is measurement data, wherein the execution of the remote machine executable instructions further causes the remote computational system to reconstruct a preliminary medical image from the medical image data before all portions of the feature vector have been received.

8. The medical system of claim 6, wherein the medical image data is a medical image, wherein execution of the machine executable instructions further causes the computational system to render the approximation of the medical image data.

9. The medical system of claim 8, wherein the assembly of the received portions of the feature vector, the approximation of the medical image data and rendering of the approximation of the medical image data is repeated multiple times before reception of all portions of the feature vector have been received at the remote computational system, wherein execution of the remote machine executable instructions further causes the remote computational system to:

receive a halt transmission instruction in response to displaying the rendering of the approximation of the medical image data; and transmit the halt transmission instruction to the local computational system via the network connection;

wherein execution of the local executable machine executable instructions further causes the local computational system to:

receive the halt transmission instruction via the network connection; and halt the transmission of the portions of the feature vector in response to receiving the halt transmission instruction.

10. A medical system comprising: a remote memory storing remote machine executable instructions and a decoder neural network being a decoder portion of an autoencoder, wherein the decoder neural network is configured to output an approximation of a medical image data in response to receiving at least a part of a feature vector descriptive of the medical image data as input, wherein the feature vector comprises a ranking assigning an importance to each of a plurality of elements of the feature vector, and wherein and the feature vector and the ranking is determined in response to inputting the medical image data into an encoder neural network being an encoder portion of the autoencoder in a local computational system, wherein one or more of the plurality of elements are assigned a ranking of higher importance than one or more other of the plurality of elements, wherein the ranking comprises an assignment of the elements of the feature vector to a discrete number of storage locations, wherein the discrete number of storage locations have different data retrieval latencies, and wherein a lower data retrieval latency is equivalent to a higher ranking; and a remote computational system, wherein execution of the remote machine executable instructions causes the remote computational system to:

sequentially receive portions of the feature vector via the network connection, wherein the portions of the feature vector with a higher importance are transmitted and received first;

assemble the received portions of the feature vector into the part of the feature vector;

receive an approximation of the medical image data in response to inputting to the part of the feature vector into the decoder neural network of the autoencoder, and wherein the part of the feature vector is input into the decoder neural network before all portions of the feature vector have been received, wherein the feature vector is received by retrieving the portions of the feature vector from the discrete number of storage locations according to the ranking.

11. A non-transitory computer-readable storage medium computer program comprising local machine executable instructions for execution by a local computational system, wherein execution of the machine executable instructions further causes the local computational system to: receive medical image data; receive a feature vector in response to inputting the medical image data into an encoder neural network being an encoder portion of an autoencoder; determine and assign a ranking of importance to each of a plurality of elements of the feature vector, wherein one or more of the plurality of elements are assigned a ranking of higher importance than one or more other of the plurality of elements, wherein the ranking comprises an assignment of the elements of the feature vector to a discrete number of storage locations, wherein the discrete number of storage locations have different data retrieval latencies, and wherein a lower data retrieval latency is equivalent to a higher ranking;

receive the feature vector descriptive of the medical image data, wherein the feature vector is configured to be input into a decoder neural network being a decoder portion of the autoencoder, wherein the decoder neural network is configured to output an approximation of the medical image data when receiving at least a part of the feature vector as input, wherein the feature vector comprises the ranking assigning an importance to the elements of the feature vector; and sequentially transmit portions of the feature vector to a remote computational system via a network connection, wherein the portions of the features vector with a higher importance are transmitted first, wherein the feature vector is received by retrieving the portions of the feature vector from the discrete number of storage locations according to the ranking.

12. A medical imaging method, comprising: wherein the method comprises: receiving medical image data; receiving a feature vector in response to inputting the medical image data into an encoder neural network being an encoder portion of an autoencoder; determining and assigning a ranking of importance to each of a plurality of elements of the feature vector, wherein one or more of the plurality of elements are assigned a ranking of higher importance than one or more other of the plurality of elements, wherein the ranking comprises an assignment of the elements of the feature vector to a discrete number of storage locations, wherein the discrete number of storage locations have different data retrieval latencies, and wherein a lower data retrieval latency is equivalent to a higher ranking; receiving the feature vector descriptive of the medical image data by a local computational system, wherein the feature vector is configured to be input into a decoder neural network being a decoder portion of the autoencoder, wherein the decoder neural network is configured to output an approximation of the medical image data when receiving at least a part of the feature vector as input, wherein the feature vector comprises the ranking assigning an importance to elements of the feature vector; and sequentially transmitting portions of the feature vector to a remote computational system via a network connection by the local computational system, wherein the portions of the features vector with a higher importance are transmitted first;

sequentially receiving the portions of the feature vector via the network connection by the remote computational system;

assemble received portions of the feature vector into the part of the feature vector by the remote computational system; and receiving the approximation of the medical image data in response to inputting to the part of the feature vector into the decoder neural network by the remote computational system, and wherein the received portions of the feature vector is input into the decoder neural network before all portions of the feature vector have been received, wherein the feature vector is received by retrieving the portions of the feature vector from the discrete number of storage locations according to the ranking.

13. The method of claim 12, wherein the determination of the ranking comprises:

determining a magnitude of the elements of the feature vector; and assigning a ranking to the elements of the feature vector that increases when the magnitude increases.

14. The method of claim 13, wherein the importance map neural network is implemented as any one of the following: incorporated into the encoder neural network or as a separate neural network.

15. The method of claim 12, further comprising an importance map neural network configured for receiving the medical image data as input and in response providing as output an assignment of the ranking to the elements of the feature vector, wherein receiving comprises receiving the ranking of the elements of the feature vector from the importance map neural network in response to inputting the medical image data into the importance map neural network.

16. The method of claim 12, wherein the ranking comprises an array of values that assigns the ranking to the elements of the feature vector.

17. The method of claim 12, wherein the ranking comprises an assignment of the elements of the feature vector to a discrete number of storage locations, wherein the discrete number of storage locations have different data retrieval latencies, and wherein a lower data retrieval latency is equivalent to a higher ranking.

18. The method of claim 12, wherein the feature vector is received by retrieving portions of the feature vector from a discrete number of storage locations according to the ranking.

* * * * *